United States Patent
Mul (10) Patent No.: US 8,017,811 B2
(45) Date of Patent: *Sep. 13, 2011

(54) HYDROFORMYLATION PROCESS

(75) Inventor: Wilhelmus Peter Mul, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/600,700

(22) PCT Filed: May 22, 2008

(86) PCT No.: PCT/EP2008/056327
§ 371 (c)(1),
(2), (4) Date: Mar. 29, 2010

(87) PCT Pub. No.: WO2008/142143
PCT Pub. Date: Nov. 27, 2008

(65) Prior Publication Data
US 2010/0179233 A1    Jul. 15, 2010

(30) Foreign Application Priority Data
May 23, 2007 (EP) ..................... 07108736

(51) Int. Cl.
*C07C 45/50* (2006.01)
(52) U.S. Cl. ..................................... 568/454
(58) Field of Classification Search .................... 568/454
See application file for complete search history.

(56) References Cited

U.S. PATENT DOCUMENTS

| | | | |
|---|---|---|---|
| 2,809,220 A | 10/1957 | Mertzweiller et al. | 260/638 |
| 3,113,974 A | 12/1963 | Heimsch | 260/632 |
| 3,351,666 A | 11/1967 | Mertzweiller et al. | 260/604 |
| 3,369,050 A | 2/1968 | Greene | 260/632 |
| 3,420,898 A | 1/1969 | Van Winkle et al. | 260/632 |
| 3,440,291 A | 4/1969 | Van Winkle et al. | 260/632 |
| 3,448,157 A | 6/1969 | Slaugh et al. | 260/604 |
| 3,448,158 A | 6/1969 | Slaugh et al. | 260/604 |
| 3,501,515 A | 3/1970 | Van Winkle et al. | 260/439 |
| 3,950,439 A | 4/1976 | Macaluso, Sr. | 260/632 |
| 4,401,834 A | 8/1983 | King | 568/881 |
| 4,447,661 A | 5/1984 | Hoshiyama et al. | 568/882 |
| 4,982,031 A | 1/1991 | Chen | 208/324 |
| 5,112,519 A | 5/1992 | Giacobbe et al. | 252/174.21 |
| 6,482,992 B2 | 11/2002 | Scholz et al. | 568/451 |

FOREIGN PATENT DOCUMENTS

| | | |
|---|---|---|
| DE | 2851515 | 6/1980 |
| GB | 703491 | 2/1954 |
| GB | 740708 | 11/1955 |
| GB | 815566 | 6/1959 |
| GB | 1041101 | 9/1966 |
| JP | 55113731 | 9/1980 |
| WO | WO9811468 | 3/1998 |
| WO | WO2007003589 | 1/2007 |
| WO | WO2008074828 | 6/2008 |

OTHER PUBLICATIONS

Bahrmann, Helmut, et al.: "OXO Synthesis", Ullmann's Encyclopedia of Industrial Chemistry, 2005 Wiley-VCH Verlag, Weinheim www.mrw.interscience.wiley.com/emrw/9783527306732/ueic/article/a18_321/current/pdf.

*Primary Examiner* — Sikarl Witherspoon (57) ABSTRACT

A hydroformylation process for the production of alcohols comprising reacting, in a reactor system comprising one or more feed streams, a reaction environment and an output stream, a feedstock composition comprising a compound having at least one olefinic carbon-to-carbon bond with hydrogen and carbon monoxide in the presence of an organophosphine modified cobalt hydroformylation catalyst, wherein the hydroformylation process is carried out in the reaction environment, which comprises at least two reaction zones, wherein the at least two reaction zones comprise an earlier reaction zone and a later reaction zone, wherein the temperature of the later reaction zone is at a temperature which is at least 2° C. greater than the temperature in the earlier reaction zone, and the temperature of the later reaction zone is in the range of from 140° C. to 220° C., and the temperature of the earlier reaction zone is at least 130° C., wherein the molar ratio of hydrogen to carbon monoxide entering the earlier reaction zone is in the range of from 0.5 to 1.65, and wherein water is added into the reactor system.

17 Claims, 1 Drawing Sheet

FIGURE 1

HYDROFORMYLATION PROCESS

The present application claims priority from European Patent Application 07108736.5 filed 23 May 2007.

FIELD OF THE INVENTION

The present invention relates to a process for hydroformylating a compound having at least one olefinic carbon-to-carbon bond. In particular, the present invention relates to the production of alcohols by the addition of carbon monoxide and hydrogen to an olefinic compound in the presence of an organophosphine modified cobalt hydroformylation catalyst.

BACKGROUND OF THE INVENTION

Various processes for producing aldehyde and/or alcohol compounds by the reaction of a compound having at least one olefinic carbon-to-carbon bond with carbon monoxide and hydrogen in the presence of a catalyst are known. Typically, these reactions are performed at elevated temperatures and pressures. The aldehyde and alcohol compounds that are produced generally correspond to compounds obtained by the addition of a carbonyl or carbinol group, respectively, to an olefinically unsaturated carbon atom in the starting material with simultaneous saturation of the olefin bond. Isomerization of the olefin bond may take place to varying degrees under certain conditions; thus, as a consequence of this isomerization, a variety of products may be obtained. These processes are typically known as hydroformylation reactions and involve reactions which may be shown in the general case by the following equation:

In the above equation, each group $R^1$ to $R^4$ may independently represent an organic radical, for example a hydrocarbyl group, or a suitable atom such as a hydrogen or halogen atom, or a hydroxyl or alkoxy group. The above reaction may also be applied to a cycloaliphatic ring having an olefinic linkage, for example cyclohexene.

The catalyst employed in a hydroformylation reaction typically comprises a transition metal, such as cobalt, platinum, rhodium or ruthenium, in complex combination with carbon monoxide and ligand(s) such as an organophosphine.

Representative of the earlier hydroformylation methods which use transition metal catalysts having organophosphine ligands are described in U.S. Pat. Nos. 3,420,898, 3,501,515, 3,448,157, 3,440,291, 3,369,050 and 3,448,158.

In attempts to improve the efficiency of a hydroformylation process, attention has typically focussed on developing novel catalysts and novel processes for recovering and re-using the catalyst. In particular, novel catalysts have been developed which may exhibit improved stability at the required high reaction temperatures. Catalysts have also been developed which may permit the single-stage production of alcohols rather than a two-step procedure involving separate hydrogenation of the intermediate aldehyde. Moreover, homogeneous catalysts have been developed which may permit improved reaction rates whilst providing acceptable yields of the desired products.

Although organophosphine modified cobalt catalysts are known to be excellent catalysts in a single step hydroformylation reaction of olefinic compounds to alcohols, the use of such catalysts can also lead to the production of paraffins as a by-product. These paraffin by-products have very little commercial value. Also, in such reactions heavy organic materials ('heavy ends') may be produced as by-products. These by-products result in waste of reactants and require additional energy in order to separate them from the product stream. Further, in order to control the amount of heavy ends in the reactor system, they may be removed via a bleed stream. Such a bleed stream will also contain catalyst and product alcohol and/or aldehyde and will thus result in the loss of expensive catalyst and valuable products. It would therefore be desirable to reduce the amount of heavy ends and paraffin by-products formed in the hydroformylation process using organophosphine modified cobalt catalysts.

Furthermore, we have detected that cobalt catalysts comprising cobalt in complex combination with carbon monoxide and an organophosphine ligand may decompose during the reaction to produce solid cobalt deposits such as cobalt and cobalt carbide (a compound of cobalt and carbon, empirical formula $CO_yC$, where y is in the range of from 2 to 3). Cobalt carbide is catalytically inactive in hydroformylation reactions. The presence of cobalt carbide also promotes further degradation of the cobalt catalyst, thereby resulting in an increased rate of catalyst usage. The cobalt carbide is not only catalytically inactive in hydroformylation reactions but also has a relatively bulky, porous structure and is insoluble in the reaction medium. This represents a significant disadvantage, particularly for homogeneous cobalt catalysts, because the cobalt carbide typically tends to agglomerate and form detrimental deposits on the internal surfaces of the production facility. The deposition of cobalt carbide impedes the running of a hydroformylation production facility with optimal efficiency. In particular, the deposition of cobalt carbide can cause plugging of the pipe work in the production facility, resulting in shut down of the production facility to allow for removal of these cobalt carbide deposits. It is known that changing conditions in a hydroformylation process can lead to an increase in the rate of degradation of the cobalt catalysts.

The present invention therefore seeks to provide a simple hydroformylation process which may be used in the single step conversion of olefinic compounds to alcohols, which not only limits the amount of paraffin and heavy ends by-products produced, but also does not cause an increase in the amount of cobalt catalyst lost through decomposition and formation of cobalt carbide and/or cobalt deposits on the internal surfaces of the production facility.

Additionally, since the demand for normal 1-alcohol products is often greater than the demand for other alcohol products, it would also therefore be desirable to increase the proportion of normal 1-alcohols in the alcohol product composition.

In a typical hydroformylation process, wherein the alcohol hydroformylation product is the desired product, a theoretical ratio of two moles of hydrogen and one mole of carbon monoxide are required to react with each mole of olefinic compound.

U.S. Pat. No. 6,482,992 describes a process for the hydroformylation of olefins to give alcohols and/or aldehydes in a plurality of hydroformylation stages, each of which comprises: a) hydroformylating olefins having a carbon atom content of 6 to 24 carbon atoms in the presence of a cobalt- or rhodium catalyst in a reactor to the point of conversion of olefin reactant to product of 20 to 98%; b) removing the catalyst from the resulting liquid discharged from the reactor;

c) separating the resulting liquid hydroformylation mixture into a low-boiler fraction comprising olefins and paraffins, and a bottoms fraction comprising aldehydes and/or alcohols; and d) reacting the olefins present in the low-boiler fraction in subsequent process stages comprising steps a, b and c and combining the bottoms fractions of process steps c) of all process stages. Different reaction conditions can be set in the hydroformylation reactors.

U.S. Pat. No. 5,112,519 describes a process for hydroformylation of olefins having the formula $(C_3)_x$, $(C_4)_x$ or mixtures thereof, where x has the value of 1 to 10, using a catalyst with a phosphine ligand at a temperature sufficient to promote reaction while retarding paraffin formation. A hydroformylation process disclosed in U.S. Pat. No. 5,112,519 is conducted in a single reactor, wherein the hydroformylation temperature is held at 135° C. for 2 hours, followed by a reaction temperature of 160° C. for 48 hours (Example 2). The reason for the use of the initially lower temperature is stated as isomerising the double bond of the olefins to the chain end.

GB 1041101 describes a hydroformylation process carried out in the presence of an unmodified cobalt catalyst with a temperature gradient across the reaction system. An amount of water of less than 10% of the total reaction mass may be added to the reaction in order to decrease the production of by-products.

The addition of a similar amount of water, preferably in the latter stages of the reaction, is taught in U.S. Pat. No. 3,113,974, as a method of improving reaction yields.

WO 98/11468 describes the injection of water into the hydrofinishing stage of a multiple-step oxo-process for alcohol production, in order to reduce heavy by-products and to permit the use of a sulfur-tolerant catalyst during hydrogenation and/or hydrofinishing.

U.S. Pat. No. 4,401,834 is directed to a process for producing alcohols, wherein in a two-step oxo-process, water is added to the aldehyde-containing product of the hydroformylation step before it undergoes hydrogenation in order to break down any acetal by-products present in the reaction mixture.

Addition of water to a hydroformylation reaction is also described in GB 740708, which is directed to the preparation of aldehydes by hydroformylation of olefins, catalysed, at least in part, by an aqueous solution of cobalt acetate. At least a portion of said aqueous solution must be injected into the reactor system at a point where an appreciable share of the olefins have been converted to aldehydes, in order to prevent flooding of the reactor system and quenching of the reaction.

According to U.S. Pat. No. 2,809,220, the addition of water to the hydrogenation environment (i.e. after formation of aldehydes in a hydroformylation process), when using a sulfactive hydrogenation catalyst, leads to an increased yield of alcohols.

The continuous recycling of water, in an amount of up to 100 to 200 wt % based on the olefin in the feed, in the carbonylation, or aldehyde synthesis reaction mixture of an oxo-process, is taught in GB 703491 as beneficial for the recycle of the catalyst and also for reaction temperature control.

DE 2851515 teaches the use of from 2 to 5 wt % water in the reaction of olefins with hydrogen and carbon monoxide, wherein formic acid ester by-products formed in the reaction are fed back to the synthesis stage in order to be decomposed.

SUMMARY OF THE INVENTION

According to the present invention, there is provided a hydroformylation process for the production of alcohols comprising reacting, in a reactor system comprising one or more feed streams, a reaction environment and an output stream, a feedstock composition comprising a compound having at least one olefinic carbon-to-carbon bond with hydrogen and carbon monoxide in the presence of an organophosphine modified cobalt hydroformylation catalyst, wherein the hydroformylation process is carried out in the reaction environment, which comprises at least two reaction zones, wherein the at least two reaction zones comprise an earlier reaction zone and a later reaction zone, wherein the temperature of the later reaction zone is at a temperature which is at least 2° C. greater than the temperature in the earlier reaction zone, and the temperature of the later reaction zone is in the range of from 140° C. to 220° C., and the temperature of the earlier reaction zone is at least 130° C., wherein the molar ratio of hydrogen to carbon monoxide entering the earlier reaction zone is in the range of from 0.5 to 1.65, and wherein water is added into the reactor system.

DETAILED DESCRIPTION OF THE INVENTION

It has now been surprisingly found that, an improved process for hydroformylation of a feedstock composition comprising a compound having at least one olefinic carbon to carbon bond, in order to form alcohols, can be achieved by the use of a reactor system comprising one or more feed streams, a reaction environment and an output stream, wherein the reaction environment comprises at least two reaction zones and the temperature of a later reaction zone is higher than the temperature of an earlier reaction zone, wherein the molar ratio of hydrogen to carbon monoxide entering the earlier reaction zone is reduced in comparison to the required theoretical ratio of 2:1, and by adding water into said reactor system.

Figure 1:
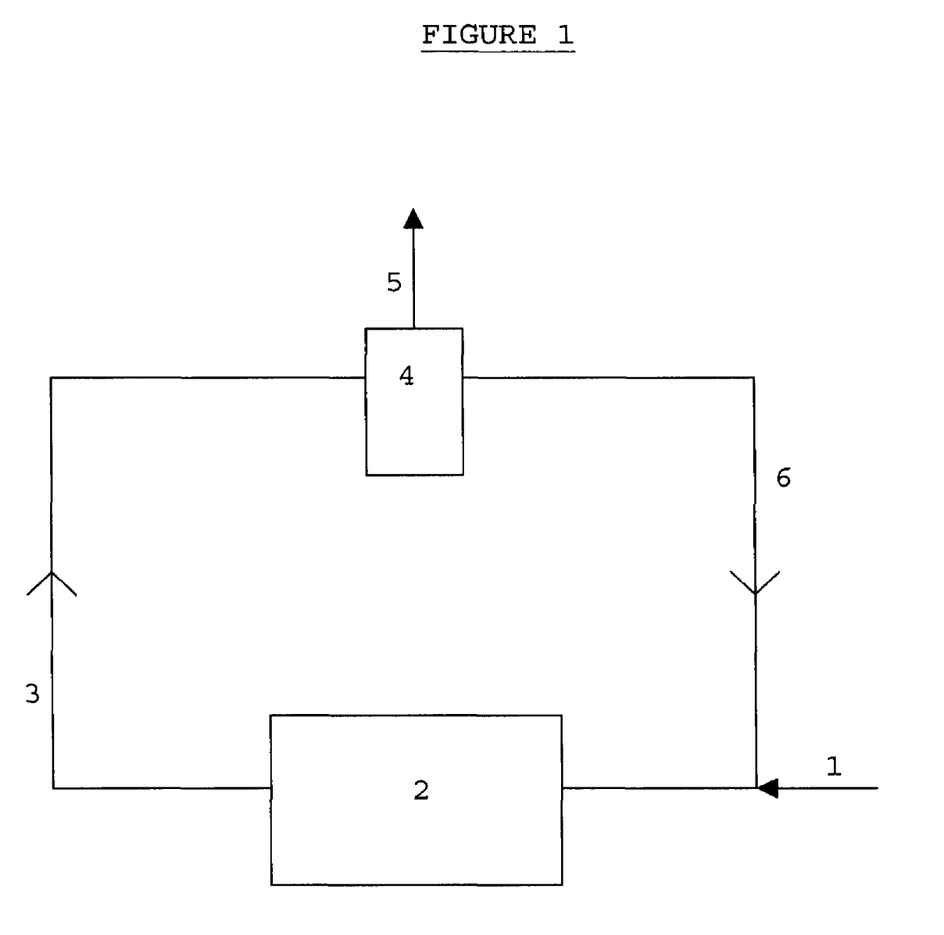
The drawing shows a schematic representation of a reactor system suitable for the process of the present invention.

The hydroformylation process of the present invention is carried out in a reactor system which comprises one or more feed streams, a reaction environment and an output stream containing crude reaction product. Preferably the process of the present invention is carried out in a reactor system as schematically shown in FIG. 1. One or more feed streams (1) are fed into the reaction environment (2). Once at least part of the olefinic feedstock has undergone a hydroformylation reaction, output stream (3) is sent to a separating means (4), which separates at least part of the crude reaction product (5) from a recycle stream (6), which is then fed back to the reaction environment (2). The hydroformylation process of the present invention may be carried out as a batch process or as a continuous process.

The reaction environment of the present invention comprises at least two reaction zones.

The term "reaction zone", as used herein, refers to a controlled environment which contains the reaction mixture, wherein the hydroformylation process of the present invention may occur. A reaction zone can be, for example, a reactor or a section of a reactor in which the reaction conditions may be controlled independently from the rest of the reactor. Typically, the reaction zones are reactors.

The number of reaction zones used in order to carry out the process of the present invention is not critical, provided that at least two reaction zones are used. Typically, the number of reaction zones used in the present invention is at most 60, preferably at most 40, more preferably at most 20, and most preferably at most 10.

When the reaction zones of the process of the present invention are reactors, the reactors may be isolated reactors or a series of reactors which are linked together. Preferably the process of the present invention is carried out in at least two reactors linked in series. By the term "linked in series" as used herein, it is meant a series of separate reaction zones which are linked together so as to form a continuous reaction chain where the reaction mixture passes continuously from one reaction zone to the next under controlled temperature and pressure conditions, wherein the temperature and pressure of the individual reaction zones may be set independently.

The at least two reaction zones used herein comprise an earlier reaction zone and a later reaction zone. The earlier reaction zone can be the first reaction zone of the process of the present invention, but could also be a later reaction zone (e.g. the second or third reaction zone). The later reaction zone can be the second reaction zone of the process of the present invention, but could alternatively be a later reaction zone (e.g. the third or fourth reaction zone). Importantly, the earlier reaction zone comes before the later reaction zone, however, the earlier reaction zone need not be immediately adjacent to the later reaction zone. For example, the earlier reaction zone may be the first reaction zone and the later reaction zone may be the second reaction zone. Alternatively, the earlier reaction zone may be the first or second reaction zone and the later reaction zone may be the fourth or fifth reaction zone. In a preferred embodiment herein, the earlier reaction zone is the first reaction zone and the later reaction zone is the second, third, fourth, fifth, sixth, seventh or eighth reaction zone.

In a particularly preferred embodiment herein, none of the reaction zones preceding the later reaction zone is at a temperature higher than 2° C. lower than the temperature of the later reaction zone.

Temperature staging is applied to the reaction zones in the process of the present invention, such that a temperature increase from a lower temperature in an earlier reaction zone to a higher temperature in a later reaction zone occurs. In particular, the temperatures of the reaction zones of the process of the present invention are controlled such that the temperature of the later reaction zone is at a temperature which is at least 2° C. greater than the temperature in the earlier reaction zone, and wherein the temperature of the later reaction zone is in the range of from 140° C. to 220° C., and the temperature of the earlier reaction zone is at least 130° C.

Preferably, the temperature of the later reaction zone will be in the range of from 145° C. to 215° C., more preferably from 150° C. to 210° C., and most preferably from 155° C. to 205° C.

The temperature of the earlier reaction zone will be at least 130° C., preferably at least 135° C., more preferably at least 140° C. The temperature of the earlier reaction zone will preferably be no more than 210° C., more preferably no more than 200° C., and even more preferably no more than 190° C. It is also required that the temperature of the earlier reaction zone will be at a temperature of at least 2° C., preferably at least 4° C., more preferably at least 6° C., most preferably at least 8° C., especially at least 10° C., lower than the temperature of the later reaction zone. Typically, the temperature of the earlier reaction zone is at most 90° C., more typically at most 80° C., commonly at most 70° C., lower than the temperature of the later reaction zone.

An example of the present invention in its simplest form would comprise only two reaction zones, wherein the first reaction zone is at a temperature of at least 130° C., for example at a temperature in the range of from 165° C. to 185° C., and the second reaction zone is at a temperature in the range of from 140° C. to 220° C., for example at a temperature in the range of from 185° C. to 205° C., wherein the temperature of the second reaction zone is at least 2° C. higher than the temperature of the first reaction zone. For example the temperature of the first reaction zone is 175° C. and the temperature of the second reaction zone is 195° C.

However, typically the present invention will comprise more than two reaction zones. For example, in an embodiment wherein the process of the present invention comprises four reaction zones, the first two reaction zones may be at a temperature of at least 130° C., for example at a temperature in the range of from 165° C. to 185° C., e.g. 180° C., and the third and fourth reaction zones may be at a temperature in the range of from 140° C. to 220° C. and which is also at least 2° C. higher than the first two reaction zones, for example at a temperature in the range of from 185° C. to 205° C., e.g. 190° C.

Overall, the process of the present invention will comprise an increase in temperature up to a maximum temperature in the range of from 140° C. to 220° C. After the maximum temperature in the range of from 140° C. to 220° C. has been attained, the temperature of any subsequent reaction zones may remain constant or be decreased.

In one embodiment of the present invention, the temperature may increase in a step-wise fashion from one reaction zone to the next; the increase in temperature may occur in a linear, asymptotic, exponential or any other manner. For example, in an embodiment wherein the process of the present invention comprises five reaction zones, the first reaction zone may be at a temperature of at least 130° C. (for example, in the range of from 150° C. to 160° C., e.g. 155° C.), the second reaction zone may be at a temperature which is higher than the first reaction zone (for example, in the range of from 160° C. to 170° C., e.g. 165° C.), the third reaction zone may be at a temperature which is higher than the second reaction zone (for example, in the range of from 170° C. to 180° C., e.g. 175° C.), the fourth reaction zone may be at a temperature which is higher than the third reaction zone (for example, in the range of from 180° C. to 190° C., e.g. 185° C.), and the fifth reaction zone may be at a temperature which is higher than the fourth reaction zone (for example, in the range of from 190° C. to 200° C., e.g. 195° C.).

In another embodiment of the present invention, the temperature of the reaction zones subsequent to the reaction zone wherein the maximum temperature has been reached is reduced relative to the maximum temperature reached. For example, in an embodiment wherein the process of the present invention comprises six reaction zones, the first two reaction zones may be at a temperature of at least 130° C., for example at a temperature in the range of from 140° C. to 160° C. (e.g. 155° C.), the third and fourth reaction zones may be at a temperature in the range of from 140° C. to 220° C. and which is also at least 2° C. higher than the first two reaction zones, for example at a temperature in the range of from 185° C. to 205° C. (e.g. 200° C.), and the fifth and sixth reaction zones may be at a temperature which is lower than the third and fourth reaction zones, for example at a temperature in the range of from 140° C. to 180° C. (e.g. 170° C.). Alternatively, in an embodiment wherein the process of the present invention comprises seven reaction zones, the first and second reaction zones may be at a temperature of at least 130° C., for example at a temperature in the range of from 165° C. to 185° C. (e.g. 180° C.), the third, fourth and fifth reaction zones may be at a temperature in the range of from 140° C. to 220° C. and which is also at least 2° C. higher than the first reaction zone, for example at a temperature in the range of from 185° C. to 205° C. (e.g. 200° C.), the sixth reaction zone may be at a temperature which is lower than the third, fourth and fifth reaction zones, for example at a temperature in the range of from 165° C. to 185° C. (e.g. 180° C.), and the seventh reaction zone may be at a temperature which is higher than the sixth reaction zone but is lower than the third, fourth and fifth reaction zones, for example at a temperature in the range of from 185° C. to 205° C. (e.g. 190° C.).

In another embodiment of the process of the present invention wherein the process comprises eight reaction zones, the first two reaction zones may be at a temperature of at least 130° C., for example at a temperature in the range of from 160° C. to 180° C. (e.g. 170° C.), the third reaction zone may be at a temperature lower than the first two reaction zones, for example at a temperature in the range of from 140° C. to 160° C. (e.g. 155° C.), the fourth, fifth and sixth reaction zones may be at a temperature in the range of from 140° C. to 220° C. and which is also at least 2° C. higher than the first two reaction zones, for example at a temperature in the range of from 180° C. to 200° C. (e.g. 195° C.), and the seventh and eighth reaction zones may be at a temperature which is lower than the fourth, fifth and sixth reaction zones for example at a temperature in the range of from 160° C. to 180° C. (e.g. 175° C.).

In an alternative embodiment, when the earlier reaction zone is preceded by at least one reaction zone, the temperature in said preceding reaction zone may optionally be lower than the minimum temperature defined for the earlier reaction zone. For example, the earlier reaction zone may be preceded by a reaction zone which is at room temperature (i.e. 25° C.). Furthermore, the use of a temperature lower than the minimum temperature defined for the earlier reaction zone in any reaction zone in the reactor series is not excluded by the present invention. However, it is preferred that the process of the present invention is performed in at least two reaction zones, wherein no reaction zone is at a temperature lower than the minimum temperature defined for the earlier reaction zone.

Since the rate of hydroformylation increases with increasing temperature, the use of the reduced temperature in the earlier reaction zone results in a decrease in overall reaction rate when compared with a hydroformylation process wherein there is no reduction in the temperature of the earlier reaction zone. The overall reaction rate also increases with increasing catalyst concentration. Therefore, any decrease in reaction rate due to the use of the reduced temperature in the earlier reaction zone can be compensated for by using an increased catalyst concentration.

The molar ratio of hydrogen to carbon monoxide entering the first reaction zone is in the range of from 0.5 to 1.65. Preferably, the molar ratio of hydrogen to olefin entering the first reaction zone is in the range of from 0.75 to 1.6. More preferably, the molar ratio of hydrogen to olefin entering the first reaction zone is in the range of from 1.0 to 1.5.

It will be understood by the skilled person that the process of the present reaction to convert olefinic feeds to alcohols will involve reaction via an intermediate aldehyde. As stated above, the theoretically ideal ratio of hydrogen to carbon monoxide in a hydroformylation reaction, wherein the intended product is an alcohol, is 2:1. Typically a slightly lower ratio (e.g. 1.8:1) of hydrogen to carbon monoxide is used in practice. However, we have now surprisingly found that, when using a ratio of hydrogen to carbon monoxide in the range of from 0.5 to 1.65 in the hydroformylation reaction of a compound having at least one olefinic carbon-to-carbon bond, to form an alcohol, which is carried out in a reactor system in which temperature staging is applied and into which water is added, a reduced yield of paraffinic and heavy ends by-products can be achieved.

The hydrogen and carbon monoxide may be introduced into the process of the present invention as two distinct streams, i.e. a hydrogen gas feed stream and a carbon monoxide gas feed stream, or as a combined feed stream, e.g. a syngas feed stream. 'Syngas' as used herein refers to a mixture of carbon monoxide and hydrogen generated, for example, by the gasification of a carbon-containing fuel.

Therefore, in the present invention, the required ratio of hydrogen to carbon monoxide entering the first reaction zone may be achieved by controlling the flow of the separate hydrogen gas feed stream or, alternatively, by providing a combined hydrogen/carbon monoxide feed stream in which the ratio of hydrogen to carbon monoxide has been determined to be in the range of from 0.5 to 1.65.

Commercially or industrially available combined hydrogen and carbon monoxide streams (e.g. syngas) generally contain a ratio of hydrogen to carbon monoxide of greater than 1.65:1. A suitable combined hydrogen/carbon monoxide feed stream may be provided by a method that reduces the level of hydrogen in the stream relative to the level of carbon monoxide in such a stream. This may involve adding carbon monoxide or removing hydrogen from the combined hydrogen and carbon monoxide stream. Hydrogen can be removed from a combined hydrogen and carbon monoxide stream by any suitable method, such as absorption or reaction.

In one embodiment of the present invention, a combined hydrogen/carbon monoxide feed stream is provided by using a combined hydrogen/carbon monoxide feed stream which comprises a combined hydrogen/carbon monoxide feed stream which has already been used in a reaction that reduces the ratio of hydrogen to carbon monoxide in said combined gas feed stream. Preferably, the combined hydrogen/carbon monoxide stream has already been subjected to a hydroformylation reaction. More preferably, the combined hydrogen/carbon monoxide stream is a recycled stream from the hydroformylation process of the present invention.

In one embodiment of the present invention, in order to provide enough hydrogen for complete reaction of the olefin to the desired alcohol product to occur, additional hydrogen may be added into the second, or a later reaction zone. This hydrogen may be added as a hydrogen gas feed stream or it may be added as a combined hydrogen/carbon monoxide feed stream (e.g. a syngas stream). The combined hydrogen/carbon monoxide feed stream added into the second or later reaction zone may contain any suitable ratio of hydrogen and carbon monoxide. Said feed stream may be the same feed stream as provided to the first reaction zone or it may be from a different source. Alternatively, in order ensure sufficient hydrogen is present for complete reaction of the olefin to the desired alcohol product to occur the ratio of carbon monoxide to olefin in the reactor system may be increased.

It will be understood by the skilled person that, as the reaction proceeds, the molar ratio of hydrogen to carbon dioxide will vary throughout the reaction environment. The ratio of hydrogen to carbon monoxide in the reaction environment may also vary if a further hydrogen gas feed stream and/or a combined hydrogen/carbon monoxide feed stream is introduced into the second and/or a later reaction zone(s).

The process of the present invention may be carried out at various pressures. Consequently, hydroformylation in accordance with the process of the present invention may typically be carried out at pressures below $8 \times 10^6$ Pa, to as low as $1 \times 10^5$ Pa. The process of the present invention is, however, not limited in its applicability to the lower pressures. Pressures in the broad range of from $1 \times 10^5$ Pa up to about $2 \times 10^7$ Pa, and in some cases up to about $2 \times 10^8$ Pa or higher, may be employed. Typically, the specific pressure used will be governed to some extent by the specific charge and catalyst employed. In general, pressures in the range of from about $2 \times 10^6$ Pa to $10 \times 10^6$ Pa and particularly in the range of from about $2.7 \times 10^6$ Pa to about $9 \times 10^6$ Pa are preferred.

The output stream from the reaction environment comprises alcohol products, aldehyde intermediates, catalyst, byproducts and any unconsumed reactants. The output stream obtained may be subjected to suitable catalyst and product separating means comprising one or more steps, for example, stratification, solvent extraction, distillation, fractionation, adsorption, filtration, etc. The specific method of product and catalyst separation employed will be governed to some extent by the specific complex and reactants charged. Catalyst or components thereof, as well as unconsumed reactants, byproducts, alcohol and aldehyde products, and solvent, when employed, may be recycled in part or its entirety to the reaction environments.

For example, a part of an alcoholic reaction product may, if desired, be recycled to the reaction environment to function as solvent and/or diluent and/or suspending medium for the catalyst, the catalyst components, and the like, passing to the reaction environments. Part of the heavy ends byproduct may also be recycled to the reaction environment in order to aid solution and/or suspension of the catalyst. Further, part or all of any aldehyde intermediates produced, may optionally be recycled to the reaction environment or may be subjected to hydrogenation or hydroformylation conditions in a separate reaction environment in the presence of a cobalt catalyst. In a preferred embodiment of the present invention, the used organophosphine-modified cobalt catalyst is recycled to the reaction environment as a feed stream for reuse.

In a preferred embodiment of the present invention, before any addition of water, the stream to be recycled comprises at most 300 ppmw, more preferably at most 100 ppmw, even more preferably at most 50 ppmw, most preferably at most 20 ppmw of water.

Additional preformed cobalt catalyst, or separate components of the catalyst capable of producing the active complex in situ, may be added to the separated material which is being recycled to the reaction environment or alternatively to the product stream exiting the reaction environment before said product stream is subjected to separating means. Further, such preformed cobalt catalyst, or separate components of the catalyst capable of producing the active complex in situ, may be added directly to the reactor or into the olefinic feed stream.

The water is preferably added into the reaction system in an amount of at least 0.05 wt %, more preferably at least 0.075 wt %, most preferably at least 0.1 wt %, based on the total weight of the reaction mixture. The water is preferably added into the reaction system in an amount of at most 10 wt %, more preferably at most 5 wt %, most preferably at most 2 wt %, based on the total weight of the reaction mixture.

In a preferred embodiment, the invention is carried out as a continuous process and water is continually added into the reactor system in order to maintain the amount of water at the desired level.

The water to be added into the reactor system may also be added to the reactor system as an aqueous solution of one or more salts. Suitable salts include, but are not limited to KOH, NaOH, NaSH and $Na_2S$.

The water may be added at any point in the reactor system. In one embodiment of the present invention, the water is added at the beginning of the reactor system. In order to achieve this, the water may be added into the reaction environment as a separate feed stream or it may be added to one of the feed streams containing one or more of the other reactants. For example, the water may be added to the recycled catalyst feed stream. Alternatively, it may be preferable to add the water to a feed stream comprising olefinic feedstock or into a feed stream comprising hydrogen or carbon monoxide.

In another embodiment of the present invention, the water is added to the reactor system at a point where at least part of the olefinic feedstock has undergone conversion to form aldehydes and/or alcohols. This involves addition of the water at a point part of the way along the reaction environment. The water may be added at the start of or part of the way along any of the reaction zones. In the case where the reaction environment comprises one or more reactors, this may be achieved by addition of the water at a point part of the way along an individual reactor, or, where there is more than one reactor, at a point between two reactors. Due to the increased solubility of water in the aldehyde intermediates and/or alcohol products in comparison to the olefinic feedstock, this embodiment has the advantage that more water may be added at this stage without risking flooding the reactor and quenching the reaction.

In a further embodiment, the water may be added to the output stream of the reactor system.

Suitably, the water is added to the reactor system while the hydroformylation reaction is proceeding.

The feed streams entering the reaction environment comprise hydrogen, carbon monoxide, olefinic feedstock, catalyst, or catalyst components, optionally one or more recycle streams, also optionally one or more dopants and, optionally, water. Suitable dopants include, but are not limited to, NaSH, $Na_2S$ and organic sulfur-containing additives including thiols, disulfides, thioethers and thiophenes. The feed streams may be introduced into the reaction environment as discreet feed streams or may be mixed together in any combination before entering the reaction environment.

Admixtures of promoters and/or stabilizers and the like may also be included in the process of the present invention. Thus, minor amounts of phenolic stabilizers such as hydroquinone and/or alkaline agents such as hydroxides of alkali metals, for example NaOH and KOH, may be added to the reaction environment.

The ratio of catalyst to the olefinic compound to be hydroformylated is generally not critical and may vary widely. It may be varied to achieve a substantially homogeneous reaction mixture. Solvents are therefore not required. However, the use of solvents which are inert, or which do not interfere to any substantial degree with the desired hydroformylation reaction under the conditions employed, may be used. Saturated liquid hydrocarbons, for example, may be used as solvent in the process, as well as alcohols, ethers, acetonitrile, sulfolane, and the like. The molar ratio of catalyst to the olefinic compound in the reaction zone at any given instant is typically at least about 1:1000000, preferably at least about 1:10000, and more preferably at least about 1:1000, and preferably at most about 10:1. A higher or lower ratio of catalyst to olefinic compound may, however, be used, but in general it will be less than 1:1.

The olefinic feedstock of the process of the present invention comprises at least one compound having at least one olefinic carbon-to-carbon bond. Commonly, the olefinic feedstock of the process of the present invention comprises more than one compound having at least one olefinic carbon-to-carbon bond. The olefinic feedstock may comprise any suitable olefinic feedstock stream, for example commercially available olefins, the product stream from a Fischer-Tropsch reaction, or an olefinic stream produced by a wax-cracking process. Suitable olefinic feedstocks may comprise as little as 10% of compounds having at least one olefinic carbon to carbon bond.

The process of the present invention is generally applicable to the hydroformylation of any optionally substituted aliphatic or cycloaliphatic compound having at least one olefinic carbon-to-carbon bond. If the aliphatic or cycloaliphatic compound having at least one olefinic carbon-to-carbon bond is substituted, the substituent will typically be inert under reaction conditions. Examples of suitable substituents include aromatic rings, alcohol groups, amine groups, silane groups and the like. Thus, the process of the present invention may be applied to the hydroformylation of olefinic compounds having, for example, from 3 to 40 carbon atoms, to produce alcohols, or under certain conditions a mixture of aldehydes and alcohols, having one more carbon atom than the starting olefinic compound. In particular, the process of the present invention may be applied to the hydroformylation of olefinic compounds having, for example, from 3 to 40 carbon atoms, to produce alcohols having one more carbon atom than the starting olefinic compound in a single step. Mono-olefinic compounds, such as propylene, butylenes, amylenes, hexylenes, heptylenes, octylenes, nonylenes, decylenes, undecylenes, dodecylenes, tridecylenes, tetradecylenes, pentadecylenes, hexadecylenes, heptadecylenes, octadecylenes, nonadecylenes, and their homologues, are examples of suitable unsaturated compounds which may be hydroformylated in the process of the present invention. Suitable unsaturated compounds include both branched and straight-chain compounds having one or more olefinic sites. When two or more double bonds are present these may be conjugated, as in 1,3-hexadiene, or non-conjugated. In the case of polyolefinic compounds, it is possible to hydroformylate only one of the olefinic sites or several or all of these sites. The unsaturated carbon-to-carbon olefinic linkages may be between terminal and their adjacent carbon atoms, as in 1-pentene, or between internal chain carbon atoms, as in 4-octene.

In one embodiment of the present invention, at least one of the compounds having at least one olefinic carbon-to-carbon bond used in the process of the present invention is a mono-olefinic compound. In another embodiment of the present invention, substantially all of the feedstock having at least one olefinic carbon-to-carbon bond comprises mono-olefinic compounds.

In another embodiment of the present invention, at least one of the compounds having at least one olefinic carbon-to-carbon bond used in the process of the present invention has an olefinic linkage between a terminal carbon atom and its adjacent carbon atom, these can also be referred to as terminal or alpha olefins. In another embodiment of the present invention, substantially all of the feedstock having at least one olefinic carbon-to-carbon bond comprise an olefinic linkage between a terminal carbon atom and its adjacent carbon atom.

In an alternative embodiment of the present invention, at least one of the compounds having at least one olefinic carbon-to-carbon bond used in the process of the present invention has an internal olefinic bond. In another alternative embodiment of the present invention, substantially all of the feedstock having at least one olefinic carbon-to-carbon bond has an internal olefinic bond.

In another embodiment of the present invention, at least one of the compounds having at least one olefinic carbon-to-carbon bond used in the process of the present invention is a linear compound having at least one olefinic carbon-to-carbon bond. In another embodiment of the present invention, substantially all of the feedstock having at least one olefinic carbon-to-carbon bond are linear compounds having at least one olefinic carbon-to-carbon bond.

In an alternative embodiment of the present invention, at least one of the compounds having at least one olefinic carbon-to-carbon bond used in the process of the present invention is a branched compound having at least one olefinic carbon-to-carbon bond. In another alternative embodiment of the present invention, substantially all of the feedstock having at least one olefinic carbon-to-carbon bond are branched compounds having at least one olefinic carbon-to-carbon bond.

By the term "substantially all" when used in relation to the feedstock composition, it is meant that at least 70 wt %, preferably at least 75 wt %, of the feedstock composition contains the specified characteristic.

Hydroformylation of macromolecular materials involving acyclic units of the above types, such as polydiolefinic compounds, for example polybutadiene, as well as copolymers of olefinic and diolefinic compounds, for example styrene-butadiene copolymer, may also be accomplished by the process of the present invention.

Cyclic compounds are equally suitable for use in the process of the present invention. Suitable cyclic compounds include unsaturated alicyclic compounds such as the cyclic olefinic compounds containing carbon-to-carbon unsaturation, such as cyclopentene, cyclohexene, and cycloheptene. Also included in this category are the terpenes and fused-ring polycyclic olefinic compounds, such as 2,5-bicyclo(2,2,1) heptadiene, 1,4,4a,5,8,8a-hexahydro-1,4,5,8-dimethanonaphthalene and the like.

The process of this invention is typically used to hydroformylate olefinic carbon-to-carbon linkages of hydrocarbon feedstock compositions but may also be used for non-hydrocarbon feedstock compositions. Thus, it is possible to hydroformylate olefinically unsaturated alcohols, ethers, epoxides, aldehydes, and acids to corresponding alcohols, ethers, aldehydes, and acids containing an aldehyde, hydroxy or alkoxy group on one of the carbon atoms previously involved in the olefinic bond of the starting material. The following are a few specific examples of different types of olefinic compounds that may be hydroformylated by the process of the present invention and the products obtained thereby:

$CH_3(CH_2)_3CH=CH_2+CO+H_2 \rightarrow CH_3(CH_2)_5CHO$
and/or $CH_3(CH_2)_5CH_2OH$+isomeric products $CH_2=CHCl+CO+H_2 \rightarrow ClCH_2CH_2CH_2OH$ and/or
$ClCH_2CH_2CHO$ $CH_3COOCH_2CH=CH_2+CO+$
$H_2 \rightarrow CH_3COOCH_2CH_2CH_2CHO$ and/or
$CH_3COOCH_2CH_2CH_2CH_2OH$ cyclopentene+$CO+H_2 \rightarrow$formylcyclopentane and/or
cyclopentylcarbinol $C_2H_5OCOCH=CHCOOC_2H_5+CO+$
$H_2 \rightarrow C_2H_5OCOCH(CHO)CH_2COOC_2H_5$ and/or
$C_2H_5OCOC(CH_2OH)HCH_2COOC_2H_5$ allyl benzene+$CO+H_2 \rightarrow$gammaphenylbutyraldehyde
and/or delta-phenylbutanol+isomeric products Typically, the olefinic feedstock of the process of the present invention comprises olefinic compounds having from 3 to 40 carbon atoms per molecule. Preferably, the feedstock composition of the process of the present invention comprises olefinic compounds having from 3 to 30 carbon atoms per molecule, more preferably having from 4 to 22 carbon atoms per molecule, and most preferably having from 5 to 20 carbon atoms per molecule. In one embodiment of the present invention, the feedstock composition comprises olefinic compounds having from 6 to 18 carbon atoms per molecule.

It will be appreciated by those skilled in the art that, depending upon the specific charge and cobalt catalyst employed, the process of the present invention may effect the direct, single stage hydroformylation of an olefinic compounds to yield a reaction product wherein the alcohols predominate over the aldehydes. By selection of reaction conditions, reaction charge and the cobalt catalyst within the above defined ranges, when using linear olefinic feedstocks, it is possible to obtain greater than or equal to 75% of straight chain alcohols, rather than various branched isomers from the hydroformylation of olefinic compounds. Typically, the alcohols are the desired end product. In the present invention, the mixture of alcohols and aldehydes in the output stream of the reactor system typically comprises at least 70% alcohols. Preferably, in the present invention, the portion of the output stream of the reactor system which consists of alcohols and aldehydes typically comprises at least 70% alcohols. More preferably, the portion of the output stream of the reactor system which consists of alcohols and aldehydes typically comprises at least 75% alcohols, most preferably at least 80% alcohols. However, by varying the operating conditions as described hereinbefore the ratio of aldehydes to alcohols in the product may be varied.

The process of the present invention may thus be employed to effect the direct, single stage hydroformylation of olefinic compounds, preferably mono-olefinic compounds, and especially mono-olefins having, for example, from 3 to 40 carbon atoms per molecule, to produce alcohols, preferably predominantly terminal alcohols having 4 to 41 carbon atoms per molecule. Olefinic fractions, such as, for example, polymeric olefinic fractions, cracked wax fractions, and the like, containing substantial proportions of olefinic compounds, may be readily hydroformylated to fractions of hydroformylated products comprising mixtures of predominantly terminal aldehydes and alcohols having one more carbon than the olefinic compounds in the charge and wherein these alcohols are the predominant reaction product. Other suitable sources of olefinic fractions include those obtained directly or indirectly from Fischer-Tropsch reactions. Suitable feeds consisting of olefinic fractions include, for example $C_7$, $C_8$, $C_9$, $C_{10}$ and higher olefinic fractions as well as olefinic fractions of wider boiling ranges such as $C_7$-$C_9$, $C_{10}$-$C_{13}$, $C_{14}$-$C_{17}$ olefinic fractions and the like. In broad terms $C_8$-$C_{16}$ olefinic compounds, in particular $C_8$-$C_{16}$ olefinic hydrocarbons, are preferred.

It will be appreciated that under the above-defined conditions, the olefinic charge may react with carbon monoxide and hydrogen to form reaction products comprising aldehydes intermediates and/or alcohol products having one more carbon atom per molecule than the olefin charged.

The organophosphine modified cobalt hydroformylation catalyst for use in the process of the present invention comprises cobalt in complex combination with carbon monoxide and an organophosphine ligand. By the term "complex combination" as used herein, is meant a coordination compound formed by the union of one or more carbon monoxide and organophosphine molecules with one or more cobalt atoms. In its active form the suitable organophosphine modified cobalt hydroformylation catalyst contains one or more cobalt components in a reduced valence state.

Suitable organophosphine ligands include those having a trivalent phosphorus atom having one available or unshared pair of electrons. Any essentially organic derivative of trivalent phosphorus with the foregoing electronic configuration is a suitable ligand for the cobalt catalyst.

Organic radicals of any size and composition may be bonded to the phosphorus atom. For example the organophosphine ligand may comprise a trivalent phosphorus having aliphatic and/or cycloaliphatic and/or heterocyclic and/or aromatic radicals satisfying its three valencies. These radicals may contain a functional group such as carbonyl, carboxyl, nitro, amino, hydroxy, saturated and/or unsaturated carbon-to-carbon linkages, and saturated and/or unsaturated non-carbon-to-carbon linkages.

It is also suitable for an organic radical to satisfy more than one of the valencies of the phosphorus atom, thereby forming a heterocyclic compound with a trivalent phosphorus atom. For example, an alkylene radical may satisfy two phosphorus valencies with its two open valencies and thereby form a cyclic compound. Another example would be an alkylene dioxy radical that forms a cyclic compound where the two oxygen atoms link an alkylene radical to the phosphorus atom. In these two examples, the third phosphorus valency may be satisfied by any other organic radical.

Another type of structure involving trivalent phosphorus having an available pair of electrons is one containing a plurality of such phosphorus atoms linked by organic radicals. This type of a compound is typically called a bidentate ligand when two such phosphorus atoms are present, a tridentate ligand when three such phosphorus atoms are present, and so forth.

Suitable organophosphine modified cobalt hydroformylation catalysts for use in the process of the present invention and their methods of preparation are disclosed in U.S. Pat. Nos. 3,369,050, 3,501,515, 3,448,158, 3,448,157, 3,420,898 and 3,440,291, all of which are incorporated herein by reference. Preferably, the organophosphine modified cobalt hydroformylation catalyst is substantially homogeneous with the reaction mixture.

Preferred organophosphine modified cobalt hydroformylation catalysts for use in the process of the present invention are those which include an organic tertiary phosphine ligand, especially a bicyclic heterocyclic tert-phosphine ligand, preferably as disclosed in U.S. Pat. No. 3,501,515. Representative examples of such ligands include:

9-hydrocarbyl-9-phosphabicyclo[4.2.1]nonane;
9-aryl-9-phosphabicyclo[4.2.1]nonane,
such as 9-phenyl-9-phosphabicyclo[4.2.1]nonane;
(di)alkyl-9-aryl-9-phosphabicyclo[4.2.11]nonane,
such as 3,7-dimethyl-9-phenyl-9-phosphabicyclo[4.2.1]-nonane, and
3,8-dimethyl-9-phenyl-9-phosphabicyclo[4.2.1]nonane;
9-alkyl-9-phosphabicyclo[4.2.1]nonane,
such as 9-octadecyl-9-phosphabicyclo[4.2.1]nonane,
9-hexyl-9-phosphabicyclo[4.2.1]nonane,
9-eicosyl-9-phosphabicyclo[4.2.1]nonane, and
9-triacontyl-9-phosphabicyclo[4.2.1]nonane;
9-cycloalkyl-9-phosphabicyclo[4.2.1]nonane,
such as 9-cyclohexyl-9-phosphabicyclo[4.2.1]nonane and
9-(1-octahydropentalyl)-9-phosphabicyclo[4.2.1]nonane;
9-cycloalkenyl-9-phosphabicyclo[4.2.1]nonane,
such as 9-cyclooctenyl-9-phosphabicyclo[4.2.1]nonane;
9-hydrocarbyl-9-phosphabicyclo[3.3.1]nonane;
9-aryl-9-phosphabicyclo[3.3.1]nonane,
such as 9-phenyl-9-phosphabicyclo[3.3.1]nonane;
di)alkyl-9-aryl-9-phosphabicyclo[3.3.1]nonane,
such as 3,7-dimethyl-9-phenyl-9-phosphabicyclo[3.3.1]-nonane and
3,8-dimethyl-9-phenyl-9-phosphabicyclo[3.3.1]nonane;
9-alkyl-9-phosphabicyclo[3.3.1]nonane, such as 9-octadecyl-9-phosphabicyclo[3.3.1]nonane,
9-hexyl-9-phosphabicyclo[3.3.1]nonane,
9-eicosyl-9-phosphabicyclo[3.3.1]nonane, and
9-triacontyl-9-phosphabicyclo[3.3.1]nonane;
9-cycloalkyl-9-phosphabicyclo[3.3.1]nonane,
such as 9-cyclohexyl-9-phosphabicyclo[3.3.1]nonane and
9-(1-octahydropentalyl)-9-phosphabicyclo[3.3.1]nonane;
9-cycloalkenyl-9-phosphabicyclo[3.3.1]nonane,
such as 9-cyclooctenyl-9-phosphabicyclo[3.3.1]nonane mixtures thereof.

A particularly preferred ligand includes a 9-eicosyl-9-phosphabicyclononane compound. A particularly preferred organophosphine modified cobalt hydroformylation catalyst includes a derivative thereof, believed to be a complex comprising cobalt.

The organophosphine modified cobalt hydroformylation catalysts can be prepared by a diversity of methods well known to those skilled in the art as disclosed in U.S. Pat. No. 3,369,050, U.S. Pat. No. 3,501,515, U.S. Pat. No. 3,448,157, U.S. Pat. No. 3,420,898 and U.S. Pat. No. 3,440,291. A convenient method is to combine a cobalt salt, organic or inorganic, with the desired phosphine ligand, for example, in liquid phase followed by reduction and carbonylation. Suitable cobalt salts comprise, for example, cobalt carboxylates such as acetates, octanoates, etc. as well as cobalt salts of mineral acids such as chlorides, fluoride, sulfates, sulfonates, etc. as well as mixtures of one or more of these cobalt salts. The valence state of the cobalt may be reduced and the cobalt-containing complex formed by heating the solution in an atmosphere of hydrogen and carbon monoxide. The reduction may be performed prior to the use of the organophosphine modified cobalt hydroformylation catalysts or it may be accomplished in-situ with the hydroformylation process in the hydroformylation environment. Alternatively, the organophosphine modified cobalt hydroformylation catalysts can be prepared from a carbon monoxide complex of cobalt. For example, it is possible to start with dicobalt octacarbonyl and, by mixing this substance with a suitable phosphine ligand, the ligand replaces one or more of the carbon monoxide molecules, producing an organophosphine modified cobalt hydroformylation catalyst; the active catalyst compound is typically formed under process conditions.

The use of the hydroformylation process of the present invention results in lower paraffin by-product formation in the overall hydroformylation process when compared with a hydroformylation process wherein there is no reduction in the temperature of the earlier reaction zone (temperature staging), no reduction in the hydrogen to carbon monoxide ratio and no water addition. The process of the present invention does not lead to high levels of heavy ends production and indeed may lead to a reduction in such by-products.

Also, it has been surprisingly observed that the use of the hydroformylation process of the present invention results in an increased proportion of normal 1-alcohols compared to other alcohols produced in the overall hydroformylation process when compared with a hydroformylation process wherein there is no reduction in the temperature of the earlier reaction zone (temperature staging), no reduction in the hydrogen to carbon monoxide ratio and no water addition. By the term "normal 1-alcohol" as used herein, it is meant the alcohol product is formed by a hydroformylation occurring upon a terminal carbon atom of the olefinic feedstock compound. In the case where the olefinic feedstock compound is a linear olefinic feedstock compound, the normal 1-alcohol would be linear 1-alcohol.

The use of the process of the present invention also does not adversely affect the stability of the catalyst used and thus does not lead to an increase in the loss of cobalt through deposition of cobalt and/or cobalt carbide on the internal walls of the reactor system.

The invention will be further described by way of the following non-limiting examples.

EXAMPLE 1

Example 1 was performed using a reactor zone which comprised four individual reactors, each of 2 liter in volume, connected in series. The olefin feedstock in Example 1 was a mixture of branched $C_{11}$ and $C_{12}$ olefins made according to the SHOP process (Shell Higher Olefin Process). A continuous stream of olefin feedstock (280 g/h), catalyst components (cobalt octoate, P-ligand (9-eicosyl-9-phosphabicyclononane) from Shell, and KOH), fresh syngas (inlet ratio $H_2/CO=1.7$) and recycle catalyst, is fed in to the first reactor. The pressure in the first reactor is maintained at $5 \times 10^6$ Pa.

After depressurization, the product alcohols, formed by hydroformylation of the olefin feed stream and the catalyst dissolved in heavy by-products are separated via a short-path distillation. The heavy-bottom stream containing the cobalt catalyst is recycled back to the first reactor, apart from a small bleed stream that is discarded. The experiment is carried out in a continuous mode.

Feed rates of catalyst components are adjusted to maintain the targeted catalyst concentration and composition: 0.25-0.3 wt % cobalt, P-ligand/Co=1.3, and KOH/Co=0.5.

Example 1 was performed using the following solutions of catalyst components: 10% wt of $Co(octoate)_2$ dissolved in the respective product alcohol, 7.5% wt of P-ligand dissolved in the respective olefin feedstock solution and 1% wt of potassium hydroxide, dissolved in the respective product alcohol. The respective product alcohol used is the alcohol composition formed by the hydroformylation of the olefin feedstock of the example. The respective olefin feedstock composition is the olefin feedstock composition used in the example.

An olefin feedstock composition comprising a mixture of linear $C_{11}$ and $C_{12}$ olefins, was hydroformylated in the reactor series described above. The concentration of cobalt in the reactor series was maintained at about 0.28% wt. based on total reactor contents. The temperature of the reactors was 192° C.

The average amount of paraffin by-product formed over the test period of 288 h was 6.9% wt on total crude alcohol product. The average amount of normal 1-alcohols produced based upon the overall amount of alcohols produced during the test period of 288 h was 81.0% wt. The average bleed rate was 1.5 wt %, based on the total olefin feed. The catalyst decomposition rate, a measure for catalyst stability, was determined to be 0.1 g Co/kg of hydroformylation products produced over the test period of 288 h.

EXAMPLES 2 TO 5

All of Examples 2 to 5 were performed using a reactor zone which comprised four individual reactors, each of 2 liter in volume, connected in series. The olefin feedstock in all of Examples 2 to 5 was a mixture of linear $C_{11}$ and $C_{12}$ olefins made according to the SHOP process (Shell Higher Olefin Process). A continuous stream of olefin feedstock (300-340 g/h), catalyst components (cobalt octoate, P-ligand (9-eicosyl-9-phosphabicyclononane) from Shell, and KOH), fresh syngas and recycle catalyst, is fed in to the first reactor. The pressure in the first reactor is maintained at $5 \times 10^6$ Pa.

After depressurization, the product alcohols, formed by hydroformylation of the olefin feed stream and the catalyst dissolved in heavy by-products are separated via a short-path distillation. The heavy-bottom stream containing the cobalt catalyst is recycled back to the first reactor, apart from a small bleed stream that is discarded. The experiment is carried out in a continuous mode.

Feed rates of catalyst components are adjusted to maintain the targeted catalyst concentration and composition: 0.22-0.27 wt % cobalt, P-ligand/Co=1.0-1.5, and KOH/Co=0.7.

All of Examples 2 to 5 were performed using the following solutions of catalyst components: 10% wt of Co(octoate)$_2$ dissolved in the respective product alcohol, 7.5% wt of P-ligand dissolved in the respective olefin feedstock solution and 1% wt of potassium hydroxide, dissolved in the respective product alcohol. The respective product alcohol used is the alcohol composition formed by the hydroformylation of the olefin feedstock of the example. The respective olefin feedstock composition is the olefin feedstock composition used in the example.

EXAMPLE 2

An olefin feedstock composition comprising a mixture of linear $C_{11}$ and $C_{12}$ olefins, was hydroformylated in the reactor series described above. The concentration of cobalt in the reactor series was maintained at about 0.25% wt. based on total reactor contents. The temperature of the first two reactors was 178° C. and the temperature of the last two reactors was 195° C. The syngas inlet ratio ($H_2$/CO) was 1.7.

The average amount of paraffin by-product formed over the test period of 312 h was 5.9% wt on total crude alcohol product. The average amount of normal 1-alcohols produced based upon the overall amount of alcohols produced during the test period of 312 h was 82.8% wt. The average bleed rate was 1.6 wt %, based on the total olefin feed.

EXAMPLE 3

An olefin feedstock composition comprising a mixture of linear $C_{11}$ and $C_{12}$ olefins, was hydroformylated in the reactor series described above. The concentration of cobalt in the reactor series was maintained at about 0.26% wt. based on total reactor contents. The temperature of the first two reactors was 178° C. and the temperature of the last two reactors was 195° C. The syngas inlet ratio ($H_2$/CO) was 1.3. The average amount of paraffin by-product formed over the test period of 279 h was 5.1% wt on total crude alcohol product. The average amount of normal 1-alcohols produced based upon the overall amount of alcohols produced during the test period of 279 h was 78.7% wt. The average bleed rate was 3.0 wt %, based on the total olefin feed. Thus a significant reduction in paraffin make was demonstrated in a reactor system which incorporated lowering of the $H_2$/CO ratio. It was noted that lowering of the $H_2$/CO ratio has not negatively affected catalyst stability during the test period of 279 h.

EXAMPLE 4

An olefin feedstock composition comprising a mixture of linear $C_{11}$ and $C_{12}$ olefins, was hydroformylated in the reactor series described above. The concentration of cobalt in the reactor series was maintained at about 0.26% wt. based on total reactor contents. The temperature of the first two reactors was 178° C. and the temperature of the last two reactors was 195° C. The syngas inlet ratio ($H_2$/CO) was 1.35. Water was dosed into a feed stream comprising olefin feedstock, before said feed stream entered the reaction environment, in an amount of 0.24 wt %, based on the amount of crude product entering the short-path distiller.

The average amount of paraffin by-product formed over the test period of 336 h was 4.7% wt on total crude alcohol product. The average amount of normal 1-alcohols produced based upon the overall amount of alcohols produced during the test period of 336 h was 81.9% wt. The average bleed rate was 1.9 wt %, based on the total olefin feed. Thus a significant reduction in paraffin make, heavy ends make and bleed rate was demonstrated in a reactor system which incorporated lowering of the $H_2$/CO ratio and the addition of water, in comparison to a reactor system in which no water was added and a higher $H_2$/CO ratio was used. It was noted that the addition of water has not negatively affected catalyst stability during the test period of 336 h, either in terms of the amount of cobalt or the amount of ligand that degrades during the process.

EXAMPLE 5

An olefin feedstock composition comprising a mixture of linear $C_{11}$ and $C_{12}$ olefins, was hydroformylated in the reactor series described above. The concentration of cobalt in the reactor series was maintained at about 0.26% wt. based on total reactor contents. The temperature of the first two reactors was 178° C. and the temperature of the last two reactors was 195° C. The syngas inlet ratio ($H_2$/CO) was 1.35. Water was dosed into a feed stream comprising olefin feedstock, before said feed stream entered the reaction environment, in an amount of 0.6 wt %, based on the amount of crude product entering the short-path distiller.

The average amount of paraffin by-product formed over the test period of 504 h was 5.1% wt on total crude alcohol product. The average amount of normal 1-alcohols produced based upon the overall amount of alcohols produced during the test period of 504 h was 81.8% wt. The average bleed rate was 1.3 wt %, based on the total olefin feed. Thus a significant reduction in paraffin make, heavy ends make and bleed rate was demonstrated in a reactor system which incorporated lowering of the $H_2$/CO ratio and the addition of water in comparison to a reactor system in which no water was added and a higher $H_2$/CO ratio was used. It was noted that the addition of water has not negatively affected catalyst stability during the test period of 504 h, either in terms of the amount of cobalt or the amount of ligand that degrades during the process.

What is claimed is:

1. A hydroformylation process for the production of alcohols comprising reacting, in a reactor system comprising one or more feed streams, a reaction environment and an output stream, a feedstock composition comprising a compound having at least one olefinic carbon-to-carbon bond with hydrogen and carbon monoxide in the presence of an organophosphine modified cobalt hydroformylation catalyst, wherein the hydroformylation process is carried out in the reaction environment, which comprises at least two reaction zones, wherein the at least two reaction zones comprise an earlier reaction zone and a later reaction zone, wherein the temperature of the later reaction zone is at a temperature which is at least 2° C. greater than the temperature in the earlier reaction zone, and the temperature of the later reaction zone is in the range of from 140° C. to 220° C., and the temperature of the earlier reaction zone is at least 130° C., wherein the molar ratio of hydrogen to carbon monoxide entering the earlier reaction zone is in the range of from 0.5 to 1.65, the pressure is at most $10 \times 10^6$ Pa, and wherein water is added into the reactor system.

2. The process of claim 1, wherein the temperature of the later reaction zone is in the range of from 145° C. to 215° C.

3. The process of claim 1, wherein the temperature of the later reaction zone is in the range of from 150° C. to 210° C.

4. The process of claim 1, wherein the temperature of the earlier reaction zone is at least 135° C.

5. The process of claim 1, wherein the temperature of the earlier reaction zone is at least 140° C.

6. The process of claim 1, wherein the amount of water added is in the range of from 0.05 to 10wt % based on the overall weight of the one or more feed streams.

7. The process of claim 1, wherein water is added at the beginning of the reactor system.

8. The process of claim 1, wherein water is added to the reactor system at a point where at least part of the feedstock composition has undergone conversion to aldehydes and/or alcohols.

9. The process of claim 1, wherein water is added to the output stream of the reactor system.

10. The process of claim 1, wherein the organophosphine modified cobalt hydroformylation catalyst comprises cobalt in complex combination with carbon monoxide and an organophosphine ligand, wherein the organophosphine ligand has a trivalent phosphorus atom having one available or unshared pair of electrons.

11. The process of claim 1, wherein the organophosphine ligand is a bicyclic heterocyclic tert-phosphine ligand.

12. The process of claim 1, wherein the ratio of hydrogen to carbon monoxide entering the first reaction zone is in the range of from 0.75 to 1.6.

13. The process of claim 1, wherein a further feed stream, comprising hydrogen, is added into the second or later reaction zone.

14. The process of claim 1, wherein a further feed stream, comprising hydrogen and carbon monoxide, is added into the second or later reaction zone.

15. The process of claim 1, wherein the process is carried out at a pressure in the range of from 100 to $2 \times 10^5$ kPa.

16. The process of claim 1, wherein the compounds having at least one olefinic carbon-to-carbon bond are linear compounds having at least one olefinic carbon-to-carbon bond.

17. The process of claim 1, wherein the feedstock composition comprises olefinic compounds having from 6 to 18 carbon atoms.

* * * * *